US007812082B2

(12) United States Patent
McIntosh et al.

(10) Patent No.: US 7,812,082 B2
(45) Date of Patent: *Oct. 12, 2010

(54) THERMOPLASTIC COATED SUPERABSORBENT POLYMER COMPOSITIONS

(75) Inventors: Stan McIntosh, Greensboro, NC (US); Scott J. Smith, Greensboro, NC (US); Angela Jones Lang, High Point, NC (US); David L. Bergman, Jr., Greensboro, NC (US)

(73) Assignee: Evonik Stockhausen, LLC, Greensboro, NC (US)

( * ) Notice: Subject to any disclaimer, the term of this patent is extended or adjusted under 35 U.S.C. 154(b) by 213 days.

This patent is subject to a terminal disclaimer.

(21) Appl. No.: 11/301,359

(22) Filed: Dec. 12, 2005

(65) Prior Publication Data

US 2007/0135554 A1 Jun. 14, 2007

(51) Int. Cl.
*B60C 1/00* (2006.01)
*C08K 3/34* (2006.01)
(52) U.S. Cl. .................. 524/492; 604/367; 604/368; 442/414
(58) Field of Classification Search .............. 604/1–3, 604/367, 368; 524/492; 442/414
See application file for complete search history.

(56) References Cited

U.S. PATENT DOCUMENTS

| 4,076,663 | A | * | 2/1978 | Masuda et al. ........... 525/54.31 |
| 4,392,908 | A | | 7/1983 | Dehnel |
| 5,032,628 | A | | 7/1991 | Choi et al. |
| 5,368,918 | A | | 11/1994 | Harada et al. |
| 5,407,442 | A | | 4/1995 | Karapasha |
| 5,409,771 | A | | 4/1995 | Dahmen et al. |
| 5,420,218 | A | | 5/1995 | Toribuchi et al. |
| 5,422,405 | A | | 6/1995 | Dairoku et al. |
| 5,567,744 | A | | 10/1996 | Nagata et al. |
| 5,599,335 | A | | 2/1997 | Goldman et al. |
| 5,599,763 | A | | 2/1997 | Harada et al. |
| 5,672,419 | A | | 9/1997 | Mukaida et al. |
| 5,716,707 | A | | 2/1998 | Mukaida et al. |
| 5,731,365 | A | | 3/1998 | Engelhardt et al. |
| 5,840,321 | A | | 11/1998 | Engelhardt et al. |
| 5,851,672 | A | | 12/1998 | Wang et al. |
| 5,859,074 | A | | 1/1999 | Rezai et al. |

(Continued)

FOREIGN PATENT DOCUMENTS

AU  6650181 A  7/1981

(Continued)

OTHER PUBLICATIONS

Malcolm P. Stevens, Polymer Chemistry An Introduction, book, 1990, pp. 3-12, Second Edition, Oxford University Press, New York, New York.
Jacqueline I. Kroschwitz, Concise Encyclopedia of Polymer Science and Engineering, book, 1990, pp. 213-219, John Wiley & Sons, Inc.
International Search Report mailed on Jun. 11, 2007 in PCT/US2006/061859.
Written Opinion of the International Searching Authority mailed on Jun. 11, 2007 in PCT/US2006/061859.

(Continued)

*Primary Examiner*—Melanie J Hand
(74) *Attorney, Agent, or Firm*—Smith Moore Leatherwood LLP

(57) ABSTRACT

The invention relates to absorptive, crosslinked polymers which are based on partly neutralized, monoethylenically unsaturated monomer carrying acid groups wherein the absorptive crosslinked polymer may be coated with a thermoplastic polymer, and have improved properties, in particular in respect of their capacity for transportation of liquids in the swollen state, and which has a high gel bed permeability and compatibility to affix to a thermoplastic material.

26 Claims, 1 Drawing Sheet

U.S. PATENT DOCUMENTS

| | | | |
|---|---|---|---|
| 5,994,440 A | 11/1999 | Staples et al. | |
| 6,027,536 A | 2/2000 | Westerink et al. | |
| 6,072,024 A | 6/2000 | Irizato et al. | |
| 6,072,101 A | 6/2000 | Beihoffer et al. | |
| 6,090,875 A | 7/2000 | Staples et al. | |
| 6,124,391 A | 9/2000 | Sun et al. | |
| 6,245,693 B1 | 6/2001 | Gagliardi et al. | |
| 6,375,644 B2 | 4/2002 | Mizutani | |
| 6,376,011 B1 | 4/2002 | Reeves et al. | |
| 6,423,046 B1 | 7/2002 | Fujioka et al. | |
| 6,441,266 B1 | 8/2002 | Dyer et al. | |
| 6,495,612 B1 | 12/2002 | Corzani et al. | |
| 6,498,201 B1 | 12/2002 | Corzani et al. | |
| 6,534,561 B1 | 3/2003 | Corzani et al. | |
| 6,534,572 B1 | 3/2003 | Ahmed et al. | |
| 6,716,514 B2 | 4/2004 | Nissing | |
| 6,730,057 B2 | 5/2004 | Zhao et al. | |
| 6,867,345 B2 | 3/2005 | Shimoe et al. | |
| 2001/0049514 A1 | 12/2001 | Dodge, II et al. | |
| 2002/0039869 A1 | 4/2002 | Achille | |
| 2002/0045869 A1 | 4/2002 | Dodge, II et al. | |
| 2002/0090453 A1 | 7/2002 | Muthiah et al. | |
| 2003/0012928 A1 | 1/2003 | Malowaniec et al. | |
| 2003/0040729 A1 | 2/2003 | Malowaniec et al. | |
| 2003/0065296 A1 | 4/2003 | Kaiser et al. | |
| 2003/0088220 A1 | 5/2003 | Molander et al. | |
| 2003/0093051 A1 | 5/2003 | Malowaniec et al. | |
| 2003/0109628 A1 | 6/2003 | Bonfanti et al. | |
| 2003/0134552 A1 | 7/2003 | Mehawej et al. | |
| 2003/0157318 A1* | 8/2003 | Brehm et al. | 428/327 |
| 2003/0175418 A1 | 9/2003 | Muthiah et al. | |
| 2003/0207639 A1 | 11/2003 | Lin | |
| 2004/0054343 A1 | 3/2004 | Barnett et al. | |
| 2004/0058159 A1 | 3/2004 | Gagliardi et al. | |
| 2004/0078015 A1 | 4/2004 | Copat et al. | |
| 2004/0121681 A1 | 6/2004 | Lindsay et al. | |
| 2004/0180998 A1 | 9/2004 | Gonzales et al. | |
| 2004/0214499 A1* | 10/2004 | Qin et al. | 442/414 |
| 2004/0222553 A1 | 11/2004 | Desai et al. | |
| 2004/0236295 A1 | 11/2004 | Muthiah et al. | |
| 2005/0013992 A1* | 1/2005 | Azad et al. | 428/327 |
| 2005/0043696 A1 | 2/2005 | Schmidt et al. | |
| 2005/0065237 A1 | 3/2005 | Schmidt et al. | |
| 2005/0096435 A1* | 5/2005 | Smith et al. | 525/244 |
| 2006/0289349 A1* | 12/2006 | Hughes | 210/500.1 |

FOREIGN PATENT DOCUMENTS

| | | | |
|---|---|---|---|
| AU | 8744198 A | 4/1999 | |
| CA | 2154425 A1 | 1/1996 | |
| CA | 2180590 A1 | 1/1997 | |
| CA | 2303298 A1 | 3/1999 | |
| CA | 2273507 A1 | 12/1999 | |
| CA | 2291997 A1 | 6/2000 | |
| CA | 2293864 A | 6/2000 | |
| CA | 2414197 A1 | 1/2002 | |
| DE | 2222780 | 11/1973 | |
| DE | 19939662 A1 | 2/2001 | |
| DE | 10010269 C1 | 7/2001 | |
| DE | 10026861 A1 | 12/2001 | |
| EP | 0478150 A2 | 4/1992 | |
| EP | 0575143 A2 | 12/1993 | |
| EP | 0612533 A1 | 8/1994 | |
| EP | 0744967 A1 | 12/1996 | |
| EP | 0850617 A1 | 7/1998 | |
| EP | 0612533 B1 | 11/1999 | |
| EP | 0963760 A1 | 12/1999 | |
| EP | 1259205 A1 | 11/2002 | |
| EP | 1259206 A1 | 11/2002 | |
| EP | 1259207 A1 | 11/2002 | |
| EP | 1350869 A1 | 10/2003 | |
| EP | 1354926 | 10/2003 | |
| EP | 1359240 A1 | 11/2003 | |
| EP | 1402905 A1 | 3/2004 | |
| EP | 1433450 A1 | 6/2004 | |
| EP | 1503812 A1 | 2/2005 | |
| FR | 2838445 A1 | 10/2003 | |
| GB | 9011250 D DO | 7/1990 | |
| JP | 2242858 | 9/1990 | |
| JP | 2002/346381 | 12/2002 | |
| JP | 2004/298384 | 10/2004 | |
| WO | WO 91/18042 A | 11/1991 | |
| WO | WO 96/14885 A1 | 5/1996 | |
| WO | WO 98/45466 A1 | 10/1998 | |
| WO | WO 99/57201 A1 | 11/1999 | |
| WO | WO 00/62922 A1 | 10/2000 | |
| WO | WO 03/043670 A1 | 5/2003 | |
| WO | WO 03/092757 | 11/2003 | |
| WO | WO 03/106162 A1 | 12/2003 | |
| WO | WO 2004/009683 | 1/2004 | |
| WO | 2004018005 A1 | 3/2004 | |
| WO | 2004018006 A1 | 3/2004 | |
| WO | WO 2004/096301 | 11/2004 | |
| WO | WO 2004/098475 A1 | 11/2004 | |
| WO | WO 2005/011860 | 2/2005 | |
| WO | WO 2005/014067 A1 | 2/2005 | |
| WO | WO 2005/014697 A1 | 2/2005 | |

OTHER PUBLICATIONS

Chem. Crete Data Sheet for AEROSIL 200 silica powder product, published by Saudi Chem Crete Co. LTD. Available at http://www.saudichemcrete.com/Cat-11/AERO200.PDF. Accessed Aug. 12, 2009. p. 1.

Loeker et al., U.S. Appl. No. 10/565,770, Final Office Action dated Aug. 18, 2009.

\* cited by examiner

THERMOPLASTIC COATED SUPERABSORBENT POLYMER COMPOSITIONS

BACKGROUND

The invention relates to superabsorbent polymer compositions which absorb water, aqueous liquids and blood wherein the superabsorbent polymer compositions of the present invention have improved properties, including high gel bed permeability, fluid retention including achieving higher gel bed permeability without the disadvantages of low retention that are characteristic of higher gel strengths, and compatibility with thermoplastics including hydrophobic thermoplastics and polyolefins. The superabsorbent polymer compositions of the present invention include a coating of a thermoplastic polymer. The present invention also relates to preparation of these superabsorbent polymer compositions and their use as absorbents in hygiene articles and in industrial fields.

Superabsorbent refers to a water-swellable, water-insoluble, organic or inorganic material capable of absorbing at least about 10 times its weight, and up to about 30 times or more its weight in an aqueous solution containing 0.9 weight percent sodium chloride solution in water. A superabsorbent polymer is a crosslinked polymer which is capable of absorbing large amounts of aqueous liquids and body fluids, such as urine or blood, with swelling and the formation of hydrogels, and of retaining them under a certain pressure in accordance with the general definition of superabsorbent. Superabsorbent polymer compositions include post treatment of the particulate polymer including surface crosslinking, surface treatment and post heat treatment. Superabsorbent polymer particles are particles of superabsorbent polymers or superabsorbent polymer compositions. The acronym SAP may be used in place of superabsorbent polymer herein.

The superabsorbent polymer compositions that are currently commercially available are crosslinked polyacrylic acids or crosslinked starch-acrylic acid graft polymers, in which some of the carboxyl groups are neutralized with sodium hydroxide solution or potassium hydroxide solution and surface treated with surface cross linker and optionally other surface additives. As a result of these characteristic properties, these polymers are chiefly used for incorporation into sanitary articles, such as babies' diapers, incontinence products or sanitary towels.

For fit, comfort and aesthetic reasons and from environmental aspects, there is an increasing trend to make sanitary articles smaller and thinner. This is being accomplished by reducing the content of the high volume fluff fiber of these articles. To ensure a constant total retention capacity of body fluids in the sanitary articles, more superabsorbent polymer content is being used in these sanitary articles. As a result of this, superabsorbent polymer compositions must have increased permeability characteristics as well as increased affinity to thermoplastic fibers such as polyolefins, which may be used to replace some or all of the fluff fiber, while retaining other characteristics such as adequate absorption and retention.

Permeability is a measure of the effective connectedness of a porous structure, be it a mat of fiber or a slab of foam or, in this case, crosslinked polymers and may be specified in terms of the void fraction and extent of connectedness of the superabsorbent polymer composition. Gel permeability is a property of the mass of particles as a whole and is related to particle size distribution, particle shape, and the connectedness of the open pores, shear modulus and surface modification of the swollen gel. In practical terms, the permeability of the superabsorbent polymer composition is a measure of how rapidly liquid flows through the mass of swollen particles. Low permeability indicates that liquid cannot flow readily through the superabsorbent polymer composition, which is generally referred to gel blocking, and that any forced flow of liquid (such as a second application of urine during use of the diaper) must take an alternate path (e.g., diaper leakage).

In particular, gel blocking is a well-known problem that may be associated with the use of superabsorbent polymer compositions in absorbent articles such as diapers. Gel blocking occurs when rapid expansion of the superabsorbent polymer particles around the point of entry of body fluid into an absorbent article causes a closing of the interstitial spaces and pores in the SAP-fluff matrix. Since the transport of liquid by diffusion through swollen hydrogel is much slower than transport through the interstitial spaces, a sealing effect occurs in the area of fluid entry. This effect is referred to as gel blocking.

Transportation of liquid through swollen superabsorbent polymer particles themselves follows the laws of diffusion and is a very slow process which plays no role in the distribution of the liquid in the use situation of the sanitary article. In superabsorbent polymer compositions, which cannot maintain an open bed structure to effect capillary transportation because of a lack of gel stability, the separation of the superabsorbent particles from one another has been ensured by embedding the superabsorbent polymer particles into a fiber matrix.

In diaper constructions, for what is called the next generation, there is less fiber material, or potentially none at all, in the absorber layer to assist in transportation of the liquid or maintenance of an open, fluid permeable structure. The superabsorbent polymer composition of these next generation diaper constructions must have a sufficiently high stability in the swollen state, generally called gel strength, so the swollen gel has a sufficient amount of capillary spaces through which liquid can be transported.

To obtain a superabsorbent polymer composition with high gel strength, the degree of crosslinking of the polymer may be increased, which necessarily results in a reduction in the swellability and the retention capacity. To achieve the increased permeabilities needed in extremely thin, next generation articles with low fiber content, current art has taught to increase the amount of crosslinking. However the absorption and retention values of the superabsorbent polymer compositions are reduced to undesirably low levels. It is an important goal of the art of making superabsorbent polymer compositions to develop a composition having a high absorption and retention capacity for liquid in the after-surface crosslinking stage and increased permeability properties. It has been found that by using new surface modifications to the superabsorbent polymer particles, results of higher permeabilities without the undesirable associated low absorption values are achieved.

Superabsorbent polymer compositions are often provided in the form of particulate powders, granules, or fibers that are distributed throughout absorbent fibrous substrate in a core to increase the absorbency of a hygiene article. One problem with the use of superabsorbents is that the superabsorbent composition can be physically dislodged from the fibrous substrate in the core of an absorbent product such as a hygiene article. Separation of the superabsorbent from its fibrous substrate may reduce the absorbency of the hygiene article and may result in superabsorbent polymer composition escaping from the article and diminishes the effectiveness of the superabsorbent polymer composition. In particular it would be advantageous to have the superabsorbent particles affix to polyolefin fibers in a hygiene article in such a fashion as to improve the superabsorbent polymer composition containment and the effectiveness of the hygiene article.

It is therefore an object of the present invention to provide an absorbing polymer composition that exhibits excellent properties such as capabilities of maintaining high liquid permeability and liquid retention even when the superabsorbent polymer is increased in percent by weight based on the absorbent structure and the composition has an acceptable affinity to fibers, especially polyolefin fibers.

SUMMARY

The present invention comprises at least a superabsorbent polymer composition including a superabsorbent polymer comprising from about 55 to about 99.9% by weight of the superabsorbent polymer of a polymerizable unsaturated acid group containing monomer and from about 0.001 to about 5% by weight of the polymerizable unsaturated acid group containing monomer of internal crosslinking agent wherein the foregoing elements are polymerized and prepared into a superabsorbent polymer particle; and the superabsorbent polymer particle is coated with from about 0.001 to about 5% by weight of the dry superabsorbent polymer composition of surface crosslinking agent; from about 0.01 to about 10% by weight of the dry superabsorbent polymer composition of a penetration modifier; from 0 to about 5% by weight of the dry superabsorbent polymer composition of a multivalent metal salt; from about 0 to 2% by weight of the dry superabsorbent polymer composition surfactant; and from about 0.01 to about 5% by weight of the dry superabsorbent polymer composition of an insoluble, inorganic powder and from about 0.01 to about 5% by weight of the dry superabsorbent polymer composition of a thermoplastic polymer having a thermoplastic melt temperature wherein the thermoplastic polymer is applied on the particle surface coincident with or followed by a temperature of the coated superabsorbent polymer particle of at least the thermoplastic melt temperature or greater, wherein the superabsorbent polymer composition exhibits a centrifuge retention capacity as measured by the Centrifuge Retention Capacity Test of about 23 g/g or more; a free swell gel bed permeability as measured by the Free Swell Gel Bed Permeability Test of about 100 Darcy or more; and a % SAP shake-out as measured by the Oven Shake-Out Procedure of 5 less than about 20%. In addition, the superabsorbent polymer composition may be post treated with a cationic polymer.

In addition the present invention is directed to absorbent compositions or sanitary articles that may contain superabsorbent polymer compositions of the present invention.

FIGURES

The foregoing and other features, aspects and advantages of the present invention will become better understood with regard to the following description, appended claims and accompanying drawings where:

DEFINITIONS

Figure 1:
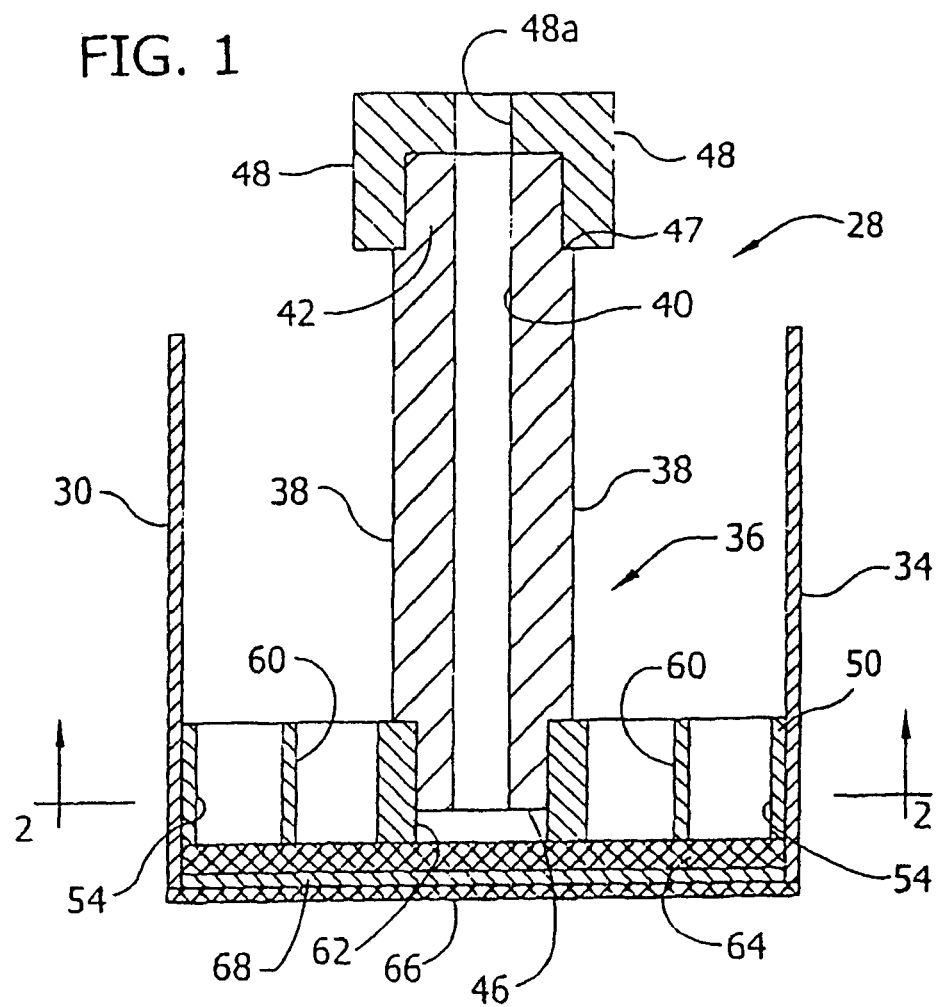
FIG. 1 is a cross-section of apparatus for conducting a Permeability Test.

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices, which can absorb and contain fluids. For example, personal care absorbent articles refer to devices, which are placed against or near the skin to absorb and contain the various fluids discharged from the body. The term "disposable" is used herein to describe absorbent articles that are not intended to be laundered or otherwise restored or reused as an absorbent article after a single use. Examples of such disposable absorbent articles include, but are not limited to, personal care absorbent articles, health/medical absorbent articles, and household/industrial absorbent articles.

The term "crosslinked" used in reference to the superabsorbent polymer refers to any means for effectively rendering normally water-soluble materials substantially water-insoluble but swellable. Such a crosslinking means can include for example, physical entanglement, crystalline domains, covalent bonds, ionic complexes and associations, hydrophilic associations such as hydrogen bonding, hydrophobic associations or Van der Waals forces.

The term "Darcy" is a CGS unit of permeability. One Darcy is the permeability of a solid through which one cubic centimeter of fluid, having a viscosity of one centipoise, will flow in one second through a section one centimeter thick and one square centimeter in cross section, if the pressure difference between the two sides of the solid is one atmosphere. It turns out that permeability has the same units as area; since there is no SI unit of permeability, square meters are used. One Darcy is equal to about $0.98692 \times 10^{-12}$ square meter or about $0.98692 \times 10^{-8}$ square centimeter.

The term "dry superabsorbent polymer composition" generally refers to the superabsorbent polymer composition having less than about 10% moisture.

The terms "hydrophilic" and "wettable" are used interchangeably to refer to a material having a contact angle of water in air of less than 90 degrees. The term "hydrophobic" refers to a material having a contact angle of water in air of at least 90 degrees. For the purposes of this application, contact angle measurements are determined as set forth in Robert J. Good and Robert J. Stromberg, Ed., in "Surface and Colloid Science—Experimental Methods," Vol. II, (Plenum Press, 1979), herein incorporated by reference in a manner consistent with the present disclosure.

The terms "particle," "particles," "particulate," "particulates" and the like, when used with the term "superabsorbent" or superabsorbent polymer" refers to the form of discrete units. The units can comprise flakes, fibers, agglomerates, granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

The term "polymers" includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible configurational isomers of the material. These configurations include, but are not limited to isotactic, syndiotactic and atactic symmetries.

The term "polyolefin" as used herein generally includes, but is not limited to, materials such as polyethylene, polypropylene, polyisobutylene, polystyrene, ethylene vinyl acetate copolymer and the like, the homopolymers, copolymers, terpolymers, etc., thereof, and blends and modifications thereof. The term "polyolefin" shall include all possible structures thereof, which includes, but is not limited to, isotatic, synodiotactic and random symmetries. Copolymers include random and block copolymers.

The terms "superabsorbent" and "superabsorbent materials" refer to water-swellable, water-insoluble organic or inorganic materials capable, under the most favorable conditions, of absorbing at least about 10 times their weight, or at least about 15 times their weight, or at least about 25 times their weight in an aqueous solution containing 0.9 weight percent sodium chloride.

The term "thermoplastic" describes a material that softens when exposed to heat and which substantially returns to a non-softened condition when cooled to room temperature.

These terms may be defined with additional language in the remaining portions of the specification.

DETAILED DESCRIPTION

A suitable superabsorbent polymer may be selected from natural, biodegradable, synthetic and modified natural polymers and materials. Superabsorbent polymers include internal crosslinking. The superabsorbent polymer composition includes surface treatment of the superabsorbent polymer as set forth herein.

In response to needs discussed above, the superabsorbent polymer composition of the present invention includes a crosslinked superabsorbent polymer comprising: a) from about 55 to about 99.9% by weight of the superabsorbent polymer of polymerizable unsaturated acid group containing monomer; b) from about 0.001 to about 5% by weight of the polymerizable unsaturated acid group containing monomer of internal crosslinking agent wherein elements a) and b) are polymerized and prepared into a superabsorbent polymer particles; wherein the superabsorbent polymer particle is surface treated with i) from about 0.001 to about 5% by weight of the dry superabsorbent polymer composition of a surface crosslinking agent; ii) from about 0.01 to about 10% by weight of the dry superabsorbent polymer composition of a penetration modifier; iii) from 0 to about 5% by weight of the dry superabsorbent polymer composition of a multivalent metal salt; iv) from about 0.01 to about 5% by weight of the dry superabsorbent polymer composition of an insoluble, inorganic powder, v) from about 0 to about 2% by weight of the dry superabsorbent polymer composition of a surfactant, and vi) from about 0.01 to 5% by weight of the dry superabsorbent polymer composition of a thermoplastic polymer wherein the surface treated superabsorbent polymer particles are heat treated.

In some aspects, the superabsorbent polymer has a degree of neutralization of more than about 25%; and the superabsorbent polymer composition has a centrifuge retention capacity as measured by the Centrifuge Retention Capacity Test of about 23 g/g or more; a free swell gel bed permeability as measured by the Free Swell Gel Bed Permeability of about 100 Darcy, such as at least about 130 Darcy or at least about 160 Darcy, or at least about 200 Darcy or more; and a % SAP shake-out as measured by the Oven Shake-Out Procedure of less than about 20%, such as less than about 16%.

As referenced above, the superabsorbent polymer composition of the present invention is obtained by the initial polymerization of from about 55 to about 99.9% by weight of the superabsorbent polymer of polymerizable unsaturated acid group containing monomer. A suitable monomer includes any of those containing carboxyl groups, such as acrylic acid, methacrylic acid or 2-acrylamido-2-methylpropanesulfonic acid, or mixtures thereof. It is desirable for at least about 50% by weight, and more desirable at least about 75% by weight of the acid groups to be carboxyl groups. The acid groups are neutralized to the extent of at least about 25-mol %, that is, the acid groups are desirably present as sodium, potassium or ammonium salts. In some aspects, the degree of neutralization can be at least about 50 mol %. In some aspects, it is desirable to utilize polymers obtained by polymerization of acrylic acid or methacrylic acid, the carboxyl groups of which are neutralized to the extent of 50-80-mol %, in the presence of internal crosslinking agents.

In some aspects, the suitable monomer that can be copolymerized with the ethylenically unsaturated monomer may include, but is not limited to acrylamide, methacrylamide, hydroxyethyl acrylate, dimethylaminoalkyl (meth)-acrylate, ethoxylated (meth)-acrylates, dimethylaminopropylacrylamide or acrylamidopropyltrimethylammonium chloride. Such monomer may be present in a range of 0 to 40% by weight of the copolymerized monomer.

As referenced above, the superabsorbent polymer of the invention also includes internal crosslinking agents. The internal crosslinking agent has at least two ethylenically unsaturated double bonds or one ethylenically unsaturated double bond and one functional group which is reactive toward acid groups of the polymerizable unsaturated acid group containing monomer or several functional groups which are reactive towards acid groups can be used as the internal crosslinking component and is desirably present during the polymerization of the polymerizable unsaturated acid group containing monomer.

Examples of internal crosslinking agents include, but are not limited to, aliphatic unsaturated amides, such as methylenebisacryl- or -methacrylamide or ethylenebisacrylamide; aliphatic esters of polyols or alkoxylated polyols with ethylenically unsaturated acids, such as di(meth)acrylates or tri (meth)acrylates of butanediol or ethylene glycol, polyglycols or trimethylolpropane; di- and triacrylate esters of trimethylolpropane which may be oxyalkylated, desirably ethoxylated, with 1 to 30 moles of alkylene oxide; acrylate and methacrylate esters of glycerol and pentaerythritol and of glycerol and pentaerythritol oxyethylated with desirably 1 to 30 mol of ethylene oxide; allyl compounds, such as allyl (meth)acrylate, alkoxylated allyl (meth)acrylate reacted with desirably 1 to 30 mol of ethylene oxide, triallyl cyanurate, triallyl isocyanurate, maleic acid diallyl ester, polyallyl esters, tetraallyloxyethane, triallylamine, tetraallylethylenediamine, diols, polyols, hydroxy allyl or acrylate compounds and allyl esters of phosphoric acid or phosphorous acid; and monomers which are capable of crosslinking, such as N-methylol compounds of unsaturated amides, such as of methacrylamide or acrylamide, and the ethers derived therefrom. Ionic crosslinkers such as multivalent metal salts may also be employed. Mixtures of the crosslinking agents mentioned can also be employed. The content of the internal crosslinking agents is from about 0.01 to about 5% by weight such as from about 0.1 to about 3% by weight based on the total amount of the polymerizable unsaturated acid group containing monomer.

In some aspects, initiators can be used for initiation of the free-radical polymerization. Suitable initiators include, but are not limited to, azo or peroxo compounds, redox systems or UV initiators, sensitizers, and/or radiation. After polymerization, the superabsorbent polymer is generally formed into particles. The superabsorbent polymer particles are surface crosslinked after polymerization by the addition of a surface crosslinking agent. In general, surface crosslinking is a process that increases the crosslink density of the polymer matrix in the vicinity of the superabsorbent particle surface with respect to the crosslinking density of the particle interior. The superabsorbent polymer particles are typically surface crosslinked by the addition of a surface crosslinking agent. In some particular aspects, desirable surface crosslinking agents include chemicals with one or more functional groups, which are reactive toward pendant groups of the polymer chains, typically the acid groups. The surface crosslinking agent may be present in an amount of from about 0.01 to about 5% by weight of the dry superabsorbent polymer composition, and such as from about 0.1 to about 3% by weight, based on the weight of the dry superabsorbent polymer composition. A heating step is preferred after addition of the surface crosslinking agent.

In one particular aspect, the particulate superabsorbent polymer is coated or surface treated with an alkylene carbonate followed by heating to effect surface crosslinking, which can improve the surface crosslinking density and the gel strength characteristics. More specifically, the surface crosslinking agent is coated onto the particulate by mixing the polymer with an aqueous alcoholic solution of the alkylene carbonate surface crosslinking agent. The amount of alcohol is determined by the solubility of the alkylene carbonate and is kept as low as possible for technical reasons, for instance protection against explosions. Suitable alcohols are methanol, isopropanol, ethanol, butanol, or butyl glycol as well as mixtures of these alcohols. In some aspects, the solvent desirably is water, which typically is used in an amount of 0.3 to 5.0% by weight, based on the weight of the dry superabsorbent polymer. In other aspects, the alkylene carbonate surface crosslinking agent is dissolved in water without any alcohol. In still other aspects, the alkylene carbonate surface cross linking agent may be applied from a powder mixture, for example, with an inorganic carrier material, such as $SiO_2$, or in a vapor state by sublimation of the alkylene carbonate.

To achieve the desired surface crosslinking properties, the alkylene carbonate should be distributed evenly on the particulate superabsorbent polymer. For this purpose, mixing is effected in suitable mixers known in the art, such as fluidized bed mixers, paddle mixers, rotary drum mixers, or twin-worm mixers. It is also possible to carry out the coating of the particulate superabsorbent polymer during one of the process steps in the production of the particulate superabsorbent polymer. In one particular aspect, a suitable process for this purpose is the inverse suspension polymerization process.

The thermal treatment, which follows the coating treatment, is carried out as follows. In general, the thermal treatment is at a temperature of from about 100 to about 300° C. Lower temperatures are possible if highly reactive epoxide crosslinking agents are used. However, if alkylene carbonates are used, then the thermal treatment is suitably at a temperature of from about 150 to about 250° C. In this particular aspect, the treatment temperature depends on the dwell time and the kind of alkylene carbonate. For example, at a temperature of about 150° C., the thermal treatment is carried out for one hour or longer. In contrast, at a temperature of about 250° C., a few minutes (e.g., about 0.5 to about 5 minutes) are sufficient to achieve the desired surface cross-linking properties. The thermal treatment may be carried out in conventional dryers or ovens known in the art.

While particles may be used by way of example of the physical form of superabsorbent polymer composition, the invention is not limited to this form and is applicable to other forms such as fibers, foams, films, beads, rods and the like, as discussed above. In some aspects, when the superabsorbent polymer composition exists as particles or in granule form, it is desirable that these particles have a size of from about 150 μm to about 850 μm based on the sieving process that is well know in the superabsorbent industry.

In some aspects, the superabsorbent polymer compositions according to the invention can include from about 0.01 to about 10% by weight of the dry superabsorbent polymer composition of a penetration modifier, such as from about 0.01 to about 5% by weight of the dry absorbent polymer composition of a penetration modifier that is added immediately before, during or immediately after the surface crosslinking agent. Examples of penetration modifiers include compounds which after the penetration depth of surface-modifying agents into the superabsorbent polymer particles by changing the viscosity, surface tension, ionic character or adhesion of the agents or medium in which these agents are applied. Suitable penetration modifiers include but are not limited to polyethylene glycols, tetraethylene glycol dimethyl ether, monovalent metal salts, surfactants, and water soluble polymers or blends thereof. It is noted that in some aspects the nature and relation amount of the median or solvent itself used to apply the surface crosslinker agent can also act as a penetration modifier.

In some aspects, the superabsorbent polymer compositions according to the invention can include from 0 to about 5% by weight of the dry superabsorbent polymer composition, such as about 0.1 to about 5% by weight of the dry superabsorbent polymer composition of a multivalent metal salt on the surface of the superabsorbent polymer particles. In some particular aspects, the multivalent metal salt is desirably water soluble. Examples of suitable metal cations include the cations of Al, Ca, Fe, Zr, Mg and Zn. In one particular aspect, the metal cation has a valence of at least +3, with Al being most desirable. Examples of suitable anions in the multivalent metal salt include halides, chlorohydrates, sulfates, nitrates, phosphates, and acetates. In particular aspects, chlorohydrates and sulfates are more desirable. In one particular aspect, sulfates are the most desirable. For example, aluminum sulfate is may be a desirable multivalent metal salt and is readily commercially available. A suitable form of aluminum sulfate is hydrated aluminum sulfate, such as aluminum sulfate having from 12 to 14 waters of hydration, for example. In addition to the salts discussed above, mixtures of multivalent metal salts can also be employed.

The polymer and multivalent metal salt can be suitably mixed by dry blending, or by mixing in solution, using means well known to those skilled in the art. In some aspects, aqueous solutions or dispersions are desirable. With dry blending, a binder may be employed in an amount which sufficient to ensure that a substantially uniform mixture of the salt and the superabsorbent polymer is maintained. The binder may be water or a nonvolatile organic compound having a boiling point of at least about 150° C. Examples of binders include water, polyols such as propylene glycol, glycerin and poly (ethylene glycol).

In some aspects, the superabsorbent polymer compositions according to the invention can comprise include from about 0.01 to about 5% by weight of the dry superabsorbent polymer composition of water-insoluble, inorganic powder, such as from about 0.1 to about 4% by weight of water-insoluble, inorganic powder. Examples of water-insoluble, inorganic powders include silica, fumed silica, silicon dioxide, silicic acid, silicates, titanium dioxide, aluminum oxide, magnesium oxide, zinc oxide, talc, calcium phosphate, clays, diatomataceous earth, zeolites, bentonite, kaolin, hydrotalcite, activated clays, etc. The water-insoluble inorganic powder additive may be a single compound or a mixture of compounds selected from the above list. In some particular aspects, microscopic noncrystalline silicon dioxide or aluminum oxide are desirable. In some aspects, the particle diameter of the inorganic powder can be 1,000 μm or smaller, such as 100 μm or smaller.

In some aspects, the superabsorbent polymer compositions according to the invention may also include the addition of from 0 to about 5% by weight of the dry superabsorbent polymer composition of a surfactant to the polymer particle surface. In some particular aspects, the surfactants can be added immediately prior to, during or immediately after the surface crosslinking step.

Examples of suitable surfactants include anionic, nonionic, cationic and amphoteric surface active agents, such as fatty acid salts, coco amines and amides and their salts, alkylsulfuric ester salts, alkylbenzene sulfonic acid salts, dialkyl sulfo-succinate, alkyl phosphate salt, and polyoxyethylene alkyl sulfate salt; polyoxyethylene alkyl ether, polyoxyethylene alkyl phenol ether, polyoxyethylene fatty acid ester, sorbitan fatty acid ester, polyoxy sorbitan fatty acid ester, polyoxyethylene alkylamine, fatty acid esters, and oxyethyleneoxypropylene block polymer; alkyl amine salts, quaternary ammonium salts; and lauryl dimethylamine oxide. However, suitable surfactants are not restricted to those mentioned above. Such surfactants may be used individually, or in combination.

In some aspects, the superabsorbent polymer compositions may also include from 0 to about 30% by weight of the dry superabsorbent polymer composition, such as about 0.1 to about 5% by weight, of water-soluble polymers based on the total amount of the superabsorbent polymer composition, such as partly or completely hydrolyzed polyvinyl acetate, polyvinylpyrrolidone, starch or starch derivatives, polyglycols, polyethylene oxides, polypropylene oxides, or polyacrylic acids. In some particular aspects the water-soluble polymers are desirably in polymerized-in form.

In some aspects, the superabsorbent polymer composition of the present invention includes from about 0.01 to about 5% by weight of the dry superabsorbent polymer composition of a thermoplastic polymer having a thermoplastic melt temperature wherein the thermoplastic polymer is applied onto the particle surface coincident with or followed by a temperature of the treated superabsorbent polymer particle at about the thermoplastic melt temperature. In some particular aspects, the thermoplastic polymer desirably is a polymer that may be in a solid, emulsion, suspension, colloidal, or solubilized state or combinations thereof. Suitable thermoplastic polymers suitable for this invention may, include but are not limited to polyolefin, polyethylene, polyester, polyamide, polyurethane, styrene polybutadiene, linear low density polyethylene (LLDPE), ethylene acrylic acid copolymer (EAA), ethylene alkyl methacrylate copolymer (EMA), polypropylene (PP), maleated polypropylene, ethylene vinyl acetate copolymer (EVA), polyester, polyamide, and blends of all families of polyolefins, such as blends of PP, EVA, EMA, EEA, EBA, HDPE, MDPE, LDPE, LLDPE, and/or VLDPE, may also be advantageously employed. The term polyolefin as used herein is defined above. In particular aspects, ethylene acrylic acid copolymer, polyester, maleated polypropylene, and EVA are preferred thermoplastic polymers for use in the present invention. The thermoplastic polymer may be functionalized to have additional benefits such as water solubility or dispersability.

In some aspects, the superabsorbent polymer compositions can also include from 0 to about 2% by weight of the dry superabsorbent polymer composition of dedusting agents, such as hydrophilic and hydrophobic dedusting agents. Suitable dedusting agents include, but are not limited to those described in U.S. Pat. Nos. 6,090,875 and 5,994,440, each of which are hereby incorporated by reference in a manner that is consistent herewith.

In some aspects, additional surface additives may optionally be employed with the superabsorbent particles, such as odor-binding substances, such as cyclodextrins, zeolites, inorganic or organic salts and similar materials; anti-caking additives, flow modification agents and the like. In addition, surface additives may be employed that perform several roles during surface modifications. For example, a single additive may be a surfactant, viscosity modifier and react to crosslink polymer chains.

In some aspects, the present invention may further include post treating the superabsorbent polymer composition after surface treatment with up to about 5% by weight of the dry superabsorbent polymer composition, such as from about 0.1 to about 5% by weight of a cationic polymer. A cationic polymer as used herein refers to a polymer or mixture of polymers comprising a functional group or groups having a potential of becoming positively charged ions upon ionization in an aqueous solution. Suitable functional groups for a cationic polymer include, but are not limited to, primary, secondary, or tertiary amino groups, imino groups, imido groups, amido groups, and quaternary ammonium groups. Examples of synthetic cationic polymers include the salts or partial salts of poly(vinyl amines), poly(allylamines), poly (ethylene imine), poly(amino propanol vinyl ethers), poly (acrylamidopropyl trimethyl ammonium chloride), poly(diallyldimethyl ammonium chloride). Examples of natural based cationic polymers include partially deacetylated chitin, chitosan and chitosan salts. Synthetic polypeptides such as polyasparagins, polylysines, polyglutamines, polyarginines are also suitable cationic polymers.

In some aspects, the superabsorbent polymer compositions of the present invention may be, after a heat treatment step, treated with water so that the superabsorbent polymer composition has a water content of up to about 10% by weight of the superabsorbent polymer composition. This water may be added with one or more of the surface additives from above added to the superabsorbent polymer. The amount of water content, measured as "% moisture",can be measured as follows: Weigh 4.5-5.5 grams of superabsorbent polymer composition(SAP) accurately in a pre-weighed aluminum weighing pan; 2) place the SAP and pan into a standard lab oven preheated to 150° C. for 30 minutes; 3) remove and re-weigh the pan and contents; and 4) calculate the percent moisture using the following formula:

% Moisture={((pan wt.+initial SAP wt.)−(dried SAP & pan wt))*100}/dried SAP wt.

The superabsorbent polymer compositions according to the invention are desirably prepared by two methods. The composition can be prepared continuously or discontinuously in a large-scale industrial manner, the after-crosslinking according to the invention being carried out accordingly.

According to one method, the partially neutralized monomer, such as acrylic acid, is converted into a gel by free-radical polymerization in aqueous solution in the presence of crosslinking agents and any further components, and the gel is comminuted, dried, ground and sieved off to the desired particle size. This solution polymerization can be carried out continuously or discontinuously.

According to another method, inverse suspension and emulsion polymerization can also be used for preparation of the products according to the invention. According to these processes, an aqueous, partly neutralized solution of monomer, such as acrylic acid, is dispersed in a hydrophobic, organic solvent with the aid of protective colloids and/or emulsifiers and the polymerization is started by free radical initiators. The internal crosslinking agents may be either dissolved in the monomer solution and are metered in together with this, or are added separately and optionally during the polymerization. The addition of a water-soluble polymer as the graft base optionally takes place via the monomer solution or by direct introduction into the oily phase. The water is then removed azeotropically from the mixture and the polymer is filtered off and optionally dried. Internal crosslinking can be carried out by polymerizing-in a polyfunctional crosslinking agent dissolved in the monomer solution and/or by reaction of suitable crosslinking agents with functional groups of the polymer during the polymerization steps.

The result of these methods is a superabsorbent pre-product. A superabsorbent pre-product as used herein is produced by repeating all of the steps for making the superabsorbent up to and including drying the material and coarse grinding in a crusher and removing particles greater than about 850 microns and smaller than about 150 microns.

The superabsorbent polymer composition of the present invention exhibits certain characteristics, or properties, as measured by free swell Gel Bed Permeability (GBP), Gel Bed Permeability under load, Centrifuge Retention Capacity (CRC), and % SAP shake-out according to the Oven Shake-Out Procedure. The free swell Gel Bed Permeability Test (GBP), is a measurement of the permeability of a swollen bed of superabsorbent material in Darcy (e.g., separate from the absorbent structure) under a confining pressure after what is commonly referred to as "free swell" conditions. The term "free swell" means that the superabsorbent material is allowed to swell without a swell restraining load upon absorbing test solution as will be described. Gel Bed Permeability under load, "GBP(0.3psi)",means the permeability of a swollen bed of gel particles (e.g., the superabsorbent material or the absorbent material as those terms are used herein), under a confining pressure, after the superabsorbent polymer composition is allowed to under a confining pressure of about 0.3 psi.

The Centrifuge Retention Capacity Test (CRC) measures the ability of the superabsorbent composition to retain liquid therein after being saturated and subjected to centrifugation under controlled conditions. The resultant retention capacity is stated as grams of liquid retained per gram weight of the sample (g/g).

The superabsorbent polymer compositions according to the invention can be employed in many products including sanitary towels, diapers or in wound coverings, they have the property that they rapidly absorb large amounts of menstrual blood, urine or other body fluids. Since the agents according to the invention retain the absorbed liquids even under pressure and additionally are capable of distributing further liquid within the construction in the swollen state, they are more desirably employed in higher concentrations, with respect to the hydrophilic fiber material, such as fluff, when compared to conventional current superabsorbent compositions. They are also suitable for use as a homogeneous superabsorber layer without fluff content within the diaper construction, as a result of which particularly thin articles are possible. The polymers are furthermore suitable for use in hygiene articles (incontinence products) for adults.

The preparation of laminates in the broadest sense, and of extruded and coextruded, wet- and dry-bonded, as well as subsequently bonded, structures are possible as further preparation processes. A combination of these possible processes with one another is also possible.

The superabsorbent polymer compositions according to the invention may also be employed in absorbent articles that are suitable for further uses. In particular, the superabsorbent polymer compositions of this invention can be used in absorbent compositions for absorbents for water or aqueous liquids, desirably in constructions for absorption of body fluids, in foamed and non-foamed sheet-like structures, in packaging materials, in constructions for plant growing, as soil improvement agents or as active compound carriers. For this, they are processed to a web by mixing with paper or fluff or synthetic fibers or by distributing the superabsorbent polymers between substrates of paper, fluff or non-woven textiles or by processing into carrier materials.

They are further suited for use in absorbent compositions such as wound dressings, packaging, agricultural absorbents, food trays and pads, and the like.

The superabsorbent polymer compositions according to the invention show a significant improvement in permeability, i.e. an improvement in the transportation of liquid in the swollen state, while maintaining high absorption and retention capacity, as compared to known superabsorbent polymer compositions.

The present invention may be better understood with reference to the following examples.

Test Procedures

Free Swell Gel Bed Permeability Test

Figure 2:
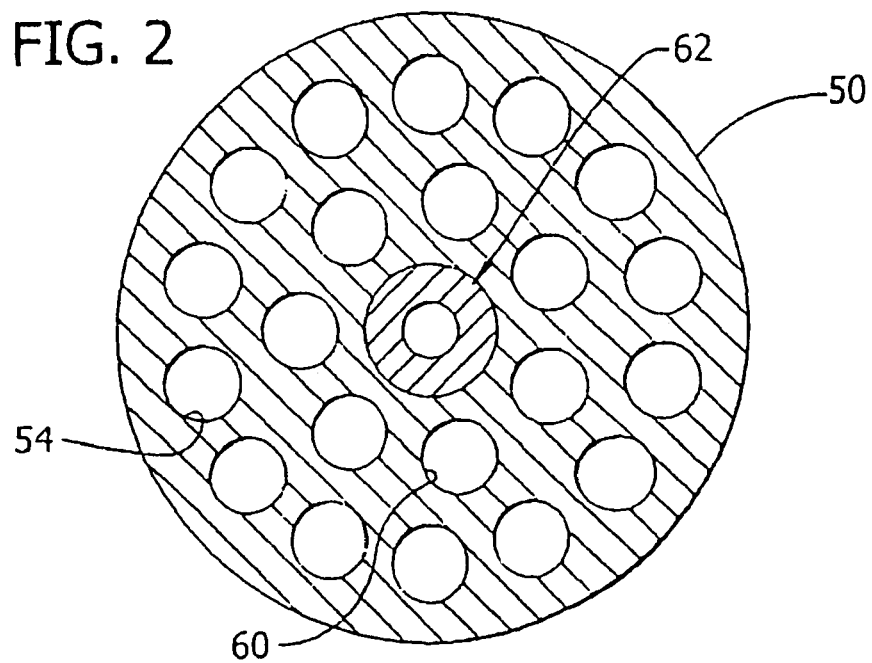
FIG. 2 is a section taken in the plane of line 2-2 of FIG. 1.

As used herein, the Free Swell Gel Bed Permeability (GBP) Test determines the permeability of a swollen bed of gel particles (e.g., such as the surface treated absorbent material or the superabsorbent material prior to being surface treated), under what is commonly referred to as "free swell" conditions. The term "free swell" means that the gel particles are allowed to swell without a restraining load upon absorbing test solution as will be described. The term "free swell" means that the superabsorbent polymer is allowed to swell without a swell restraining load upon absorbing test solution as will be described. A suitable apparatus for conducting a Permeability Test is shown in FIGS. 1 and 2 and indicated generally as 28. The test apparatus 28 comprises a sample container, generally indicated at 30, and a piston, generally indicated at 36. The piston 36 comprises a cylindrical LEXAN® shaft 38 having a concentric cylindrical hole 40 bored down the longitudinal axis of the shaft. Both ends of the shaft 38 are machined to provide upper and lower ends respectively designated 42, 46. A weight, indicated as 48, rests on one end 42 and has a cylindrical hole 48a bored through at least a portion of its center.

A circular piston head 50 is positioned on the other end 46 and is provided with a concentric inner ring of seven holes 60, each having a diameter of about 0.95 cm, and a concentric outer ring of fourteen holes 54, also each having a diameter of about 0.95 cm. The holes 54, 60 are bored from the top to the bottom of the piston head 50. The piston head 50 also has a cylindrical hole 62 bored in the center thereof to receive end 46 of the shaft 38. The bottom of the piston head 50 may also be covered with a biaxially stretched 400 mesh stainless steel screen 64.

The sample container 30 comprises a cylinder 34 and a 400 mesh stainless steel cloth screen 66 that is biaxially stretched to tautness and attached to the lower end of the cylinder. A superabsorbent polymer sample, indicated as 68 in FIG. 1, is supported on the screen 66 within the cylinder 34 during testing.

The cylinder 34 may be bored from a transparent LEXAN® rod or equivalent material, or it may be cut from a LEXAN® tubing or equivalent material, and has an inner diameter of about 6 cm (e.g., a cross sectional area of about 28.27 cm$^2$), a wall thickness of about 0.5 cm and a height of approximately 10 cm. Drainage holes (not shown) are formed in the sidewall of the cylinder 34 at a height of approximately 7.8 cm above the screen 66 to allow liquid to drain from the cylinder to thereby maintain a fluid level in the sample container at approximately 7.8 cm above screen 66. The piston head 50 is machined from a LEXAN® rod or equivalent material and has a height of approximately 16 mm and a diameter sized such that it fits within the cylinder 34 with minimum wall clearance but still slides freely. The shaft 38 is machined from a LEXAN® rod or equivalent material and has an outer diameter of about 2.22 cm and an inner diameter of about 0.64 cm.

The shaft upper end 42 is approximately 2.54 cm long and approximately 1.58 cm in diameter, forming an annular shoulder 47 to support the weight 48. The annular weight 48 has an inner diameter of about 1.59 cm so that it slips onto the upper end 42 of the shaft 38 and rests on the annular shoulder 47 formed thereon. The annular weight 48 can be made from stainless steel or from other suitable materials resistant to corrosion in the presence of the test solution, which are 0.9 weight percent sodium chloride solutions in distilled water. The combined weight of the piston 36 and annular weight 48 equals approximately 596 grams (g), which corresponds to a pressure applied to the absorbent structure sample 68 of about 0.3 pounds per square inch (psi), or about 20.7 grams/cm$^2$, over a sample area of about 28.27 cm$^2$.

When the test solution flows through the test apparatus during testing as described below, the sample container 30 generally rests on a 16 mesh rigid stainless steel support screen (not shown). Alternatively, the sample container 30 may rest on a support ring (not shown) diametrically sized substantially the same as the cylinder 34 so that the support ring does not restrict flow from the bottom of the container.

To conduct the Gel Bed Permeability Test under "free swell" conditions, the piston 36, with the weight 48 seated thereon, is placed in an empty sample container 30 and the height from the bottom of the weight 48 to the top of the cylinder 34 is measured using a caliper of suitable gauge accurate to 0.01 mm. It is important to measure the height of each sample container 30 empty and to keep track of which piston 36 and weight 48 is used when using multiple test apparatus. The same piston 36 and weight 48 should be used for measurement when the superabsorbent polymer sample 68 is water swollen following saturation.

The sample to be tested is prepared from superabsorbent material particles which are prescreened through a U.S. standard 30 mesh screen and retained on a U.S. standard 50 mesh screen. As a result, the test sample comprises particles sized in the range of about 300 to about 600 microns. The particles can be prescreened by hand or automatically. Approximately 2.0 grams of the sample is placed in the sample container 30, and the container, without the piston 36 and weight 48 therein, is then submerged in the test solution for a time period of about 60 minutes to saturate the sample and allow the sample to swell free of any restraining load.

At the end of this period, the piston 36 and weight 48 assembly is place on the saturated sample 68 in the sample container 30 and then the sample container 30, piston 36, weight 48, and sample 68 are removed from the solution. The thickness of the saturated sample 68 is determined by again measuring the height from the bottom of the weight 48 to the top of the cylinder 34, using the same caliper or gauge used previously provided that the zero point is unchanged from the initial height measurement. The height measurement obtained from measuring the empty sample container 30, piston 36, and weight 48 is subtracted from the height measurement obtained after saturating the sample 68. The resulting value is the thickness, or height "H" of the swollen sample.

The permeability measurement is initiated by delivering a flow of the test solution into the sample container 30 with the saturated sample 68, piston 36, and weight 48 inside. The flow rate of test solution into the container is adjusted to maintain a fluid height of about 7.8 cm above the bottom of the sample container. The quantity of solution passing through the sample 68 versus time is measured gravimetrically. Data points are collected every second for at least twenty seconds once the fluid level has been stabilized to and maintained at about 7.8 cm in height. The flow rate Q through the swollen sample 68 is determined in units of grams/second (g/g) by a linear least-square fit of fluid passing through the sample 68 (in grams) versus time (in seconds).

Permeability in Darcy is obtained by the following equation:

$$K=[Q*H*Mu]/[A*Rho*P]$$

where K=Permeability (cm$^2$), Q=flow rate (g/rate), H=height of sample (cm), Mu=liquid viscosity (poise) (approximately one centipoise for the test solution used with the Test), A=cross-sectional area for liquid flow (cm$^2$), Rho=liquid density (g/cm$^3$), for the test solution used with this Test) and P=hydrostatic pressure (dynes/cm$^2$) (normally approximately 3,923 dynes/cm$^2$). The hydrostatic pressure is calculated from the following equation $$P=Rho*g*h$$

where Rho=liquid density (g/cm$^3$), g=gravitational acceleration, nominally 981 cm/sec$^2$, and h=fluid height. e.g., 7.8 cm for the Permeability Test described herein.

Gel Bed Permeability Under Load Test

As used herein, the Gel Bed Permeability (GBP) Under Load Test, otherwise referred to herein as GBP at 0.3 psi, determines the permeability of a swollen bed of gel particles (e.g., the superabsorbent material or the absorbent material as those terms are used herein), under conditions that are commonly referred to as being "under load" conditions. The term "under load" means that swelling of the particles is restrained by a load generally consistent with normal usage loads applied to the particles, such as sitting, walking, twisting, etc. by the wearer.

More particularly, the Gel Bed Permeability Under Load Test is substantially the same as the Free Swell Gel Bed Permeability Test set forth previously with the following exception. After approximately 2.0 grams of the sample is placed in the sample container 30 and spread out evenly on the bottom of the sample container, the piston 36 and weight 48 are placed on the sample within the sample container prior to the sample container (with the piston and weight therein) being submerged in the test solution (0.9% by weight NaCl saline) for a time period of about 60 minutes. As a result, a 0.3 psi restraining load is applied to the sample as the sample becomes saturated and swells.

Centrifuge Retention Capacity Test

The Centrifuge Retention Capacity (CRC) Test measures the ability of the superabsorbent polymer to retain liquid therein after being saturated and subjected to centrifugation under controlled conditions. The resultant retention capacity is stated as grams of liquid retained per gram weight of the sample (g/g). The sample to be tested is prepared from particles which is pre-screened through a U.S. standard 30 mesh screen and retained on a U.S. standard 50 mesh screen. As a result, the superabsorbent polymer sample comprises particles sized in the range of about 300 to about 600 microns. The particles can be pre-screened by hand or automatically.

The retention capacity is measured by placing about 0.2 grams of the pre-screened superabsorbent polymer sample into a water-permeable bag that will contain the sample while allowing a test solution (0.9 weight percent sodium chloride in distilled water) to be freely absorbed by the sample. A heat-sealable tea bag material, such as that available from Dexter Corporation (having a place of business in Windsor Locks, Conn., U.S.A.) as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals should be about 0.25 inches inside the edge of the material. After the sample is placed in the pouch, the remaining open edge of the pouch is also heat-sealed. Empty bags are also made to serve as controls. Three samples are prepared for each superabsorbent polymer to be tested.

The sealed bags are placed submerged in a pan containing the test solution at 23° C., making sure that the bags are held down until they are completely wetted. After wetting, the samples remain in the solution for about 30 minutes, at which time they are removed from the solution and temporarily laid on a non-absorbent flat surface.

The wet bags are then placed into the basket of a suitable centrifuge capable of subjecting the samples to a g-force of about 350. One suitable centrifuge is a CLAY ADAMS DYNAC II, model #0103, having a water collection basket, a digital rpm gauge, and a machined drainage basket adapted to hold and drain the flat bag samples. Where multiple samples are centrifuged, the samples must be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed, with the empty bags (controls) being weighed first, followed by the bags containing the superabsorbent polymer samples. The amount of solution retained by the superabsorbent polymer sample, taking into account the solution retained by the bag itself, is the centrifuge retention capacity (CRC) of the superabsorbent polymer, expressed as grams of fluid per gram of superabsorbent polymer. More particularly, the retention capacity is determined by the following equation:

$$\frac{\text{sample/bag after centrifuge} - \text{empty bag after centrifuge} - \text{dry sample weight}}{\text{dry sample weight}}$$

The three samples are tested and the results are averaged to determine the retention capacity (CRC) of the superabsorbent polymer composition.

Oven Shakeout Test

The Oven Shakeout Test measures the ability of the superabsorbent polymer to affix itself to a polyolefin material. The oven shakeout test is stated as % SAP shake-out or superabsorbent composition shake-out from the polyolefin. Materials required for this test include a 4" diameter aluminum weighing pan, a polyethylene ZIPLOC® baggie, superabsorbent polymer particles (SAP), 0.5 inch aluminum plate, air convention oven, Retsch Vibro Sieving machine model number 30.403.009, a bottom pan and 12-20 mesh screen.

The aluminum plate is placed in a standard lab oven, such as a BLUE M forced air laboratory oven (available from Thermal Product Solutions, having a place of business located in Montoursville, Pa., U.S.A.) on a rack to hold the plate in a horizontal position in the central portion of the oven. The oven is preheated to 160° C. From a polyethylene ZIPLOC® baggie, a 3 inch diameter circle of polyethylene film is cut to fit the 4 inch diameter aluminum weighing pan and the combined weight of the pan and film is recorded. The weighing pan assembly is placed on top of the aluminum plate in the preheated oven and the oven door is closed. 5.0+/−0.05 grams of the superabsorbent polymer composition particles are weighed into a separate sample pan. After 5 minutes, the oven door is opened and the superabsorbent polymer particles are poured on top of the polyethylene film in the weighing pan. The weighing pan is gently shaken by the edges to ensure that the superabsorbent polymer particles are spread out over as much of the film as possible. This step needs to be completed quickly to keep the oven chamber from cooling too much. The oven door is closed for another 60 seconds. The film/pan/superabsorbent assembly is removed from the oven and placed on a suitable heat-insensitive surface in the laboratory to cool for 60 seconds. The film/pan/superabsorbent assembly is inverted to decant loose superabsorbent polymer particles that have not come into contact with polyethylene surface. The assembly is weighed and the weight is recorded as the raw pre-shake weight. The pre-shake superabsorbent weight is calculated by subtracting the initial pan/film weight from the above raw pre-shake weight. The film/pan/superabsorbent assembly is placed on the mesh screen in the Retsch Vibro with the superabsorbent facing down and vibrated for 1 minute with the vibration gauge indicating intensity just to the vertical mark labeled '1.' The film/pan/superabsorbent assembly is removed and the weight is recorded as the raw post-shake weight. The post-shake superabsorbent weight is calculated by subtracting the film/pan weight from the raw post-shake weight.

The percent superabsorbent lost is calculated by the following formula:

$$\% \text{ SAP shake-out} = 100\% * \frac{\left(\begin{array}{c}\text{pre-shake } SAP \text{ } wt - \\ \text{post-shake } SAP \text{ } wt\end{array}\right)}{(\text{pre-shake } SAP \text{ } wt)}\%$$

Minimums of three samples are tested and the results are averaged to determine the average superabsorbent composition shake-out of the sample.

EXAMPLES

The following examples are provided to illustrate the invention, and do not limit the scope of the claims. Unless otherwise stated all parts and percentages are by weight.

Example 1 Preproduct

In an insulated, flat-bottomed reaction vessel, 1866.7 g of 50% NaOH was added to 3090.26 g of distilled water and cooled to 25° C. 800 g of acrylic acid was then added to the caustic solution and the solution again cooled to 25° C. A second solution of 1600 g of acrylic acid containing 120 g of 50% by weight methoxypolyethyleneglycol monomethacrylate in acrylic acid and 14.4 g of ethoxylated trimethylolpropanetriacrylate were then added to the first solution, followed by cooling to 15° C., the addition of 14.4 g of hydroxymonoallyl ether with 10 moles of ethoxylation, and additional cooling to 5° C., all while stirring. The monomer solution was then polymerized with a mixture of 100 ppm hydrogen peroxide, 200 ppm azo-bis-(2-amidino-propene)dihydrochloride, 200 ppm sodiumpersulfate and 40 ppm ascorbic acid (all aqueous solutions) under adiabatic conditions and held near the maximum temperature ($T_{max}$) for 25 minutes. The resulting gel was chopped and extruded with a Hobart 4M6 commercial extruder, followed by drying in a Procter & Schwartz Model 062 forced air oven at 175° C. for 10 minutes with up flow and 6 minutes with down flow air on a 20 in×40 in perforated metal tray to a final product moisture level of less than 5 wt %. The dried material was coarse ground in a Prodeva Model 315-S crusher, milled in an MPI 666-F three stage roller mill and sieved with an Minox MTS 600DS3V to remove particles greater than 850 microns and smaller than 150 microns.

Comparative Example 1 and Examples 2-4

In accordance with Table 1 for Comparative Examples 1 and Examples 2 to 4, 3,000 g of the Preproduct of Example 1 were blended at ambient conditions with amounts of a 25% emulsion of maleated polypropylene as shown in Table 1. In particular, the Preproduct of Example 1 was fluidized. A spray solution was prepared containing ethylene carbonate, thermoplastic coating and water in accordance with the amounts given in Table 1. The spray solution was sprayed onto the fluidized Preproduct. The spray blend was formulated to deliver 1% EC, 0.0625% MPP, and 4% water, with the amount of water calculated to include what the MPP emulsion contributed on top of the added water. Then, 24.0 grams of fumed silica was added to the sprayed Preproduct. The total mixture was fluidized for about 1 minute. Ethylene carbonate/thermoplastic/water-coated preproduct was fed into a continuous paddle dryer for 50 minutes at 60-70 grams/minute with a 2.5-3 kg steady-state polymer mass in the reactor. The peak superabsorbent temperature was reached near the middle of the second half of the reactor, and this temperature was held to 190-195° C. Paddles were held to 25 rpm. The composition was then further treated with an aqueous solution of PEG8000.

For each Comparative Example 1 and Examples 1-3, samples were tested by the Oven Shakeout Procedure as set forth herein. The superabsorbent composition shake-out of the Comparative Examples 1 and Examples 1-3 were measured and are found in Table 2. It can be seen from Table 2, that superabsorbent polymer compositions of the present invention have lower superabsorbent composition shake-out than other superabsorbent polymer compositions of the comparative examples.

TABLE 1

Comparative Example 1 and Examples 1-3

| Comparative Example or Example | Ethylene Carbonate % on SAP | Thermoplastic Coating % on SAP | Water % on SAP | Silica % | CRC g/g | GBP 0.0 psi Darcy | GBP 0.3 psi Darcy |
|---|---|---|---|---|---|---|---|
| Comp Ex 1 | 1 | none | 4 | 0 | 25.9 | 37 | 10.23 |
| Example 1 | 1 | 0.0625 MPP[1] | 4 | 0 | 26 | 111 | 7.65 |
| Example 2 | 1 | 0.0625 MPP[1] | 4 | 0.4 | 25.7 | 152 | 16.04 |
| Example 3 | 1 | 0.0625 MPP[1] | 4 | 0.8 | 25.5 | 156 | 11.29 |

MPP[1] maleated polypropylene

TABLE 2

Superabsorbent Composition Shake-out Results for Comparative Example 1 and Examples 1-3

| Comparative Example or Example | pan + film (g) | preshake (g) | post shake (g) | % SAP retained | % SAP shake-out | % SAP Shake-out Average |
|---|---|---|---|---|---|---|
| Comp1a | 2.8381 | 4.1056 | 3.4654 | 49.49 | 50.51 | |
| Comp 1b | 2.8556 | 3.7338 | 3.4738 | 70.39 | 29.61 | 41.51 |
| Comp1c | 2.8692 | 4.1281 | 3.569 | 55.59 | 44.41 | |

TABLE 2-continued

Superabsorbent Composition Shake-out Results
for Comparative Example 1 and Examples 1-3

| Comparative Example or Example | pan + film (g) | preshake (g) | post shake (g) | % SAP retained | % SAP shake-out | % SAP Shake-out Average |
|---|---|---|---|---|---|---|
| Ex 1a | 2.8306 | 3.4794 | 3.3824 | 85.05 | 14.95 | |
| Ex 1b | 2.8203 | 3.5562 | 3.4829 | 90.04 | 9.96 | 12.88 |
| Ex 1c | 2.8604 | 3.8075 | 3.6774 | 86.26 | 13.74 | |
| Ex 2a | 2.8441 | 3.4821 | 3.3853 | 84.83 | 15.17 | |
| Ex 2b | 2.8412 | 3.2991 | 3.2691 | 93.45 | 6.55 | 7.96 |
| Ex 2c | 2.8404 | 3.2888 | 3.2468 | 90.63 | 9.37 | |
| Ex 3a | 2.8488 | 3.7219 | 3.6421 | 90.86 | 9.14 | |
| Ex 3b | 2.8357 | 3.3495 | 3.2912 | 88.65 | 11.35 | 10.32 |
| Ex 3c | 2.857 | 3.8653 | 3.7598 | 89.54 | 10.46 | |

Examples 4-5

In accordance with Table 3 for Example 4 and Example 5, 3,000 g of the Preproduct of Example 1 was blended at ambient conditions with amounts of a 25% aqueous emulsion of a blend of maleated polypropylene and ethylene acrylic acid copolymer. In particular, the Preproduct of Example 1 was fluidized. A spray solution was prepared by dissolving ethylene carbonate in warm water, adding the maleated polypropylene to the solution, then adding the ethylene acrylic acid copolymer to the solution in accordance with the amounts given in Table 3. The spray solution was sprayed onto the fluidized Preproduct. Then, 24.0 grams of fumed silica was added to the sprayed Preproduct. The total mixture was fluidized for about 1 minute. Ethylene carbonate/thermoplastic/water-coated preproduct was fed into a continuous paddle dryer for 50 minutes at 60-70 grams/minute with a 2.5-3 kg steady-state polymer mass in the reactor. The peak superabsorbent temperature was reached near the middle of the second half of the reactor, and this temperature was held to 190-195° C. Paddles were held to 25 rpm.

After surface-crosslinking using ethylene carbonate and heating, the surface treated superabsorbent composition was sprayed with a 1.25% solution of polyvinylamine to result in 0.25% polyvinylamine on superabsorbent by weight. To apply the solution, surface-crosslinked superabsorbent was fluidized and the liquid was sprayed onto the moving powder bed.

TABLE 3

Examples 4-5

| Example | Ethylene Carbonate % of SAP | Thermoplastic Coating % on SAP | Water g | Silica % | CRC g/g | GBP 0.0 psi Darcy |
|---|---|---|---|---|---|---|
| Example 4 | 1 | 0.0312% MPP[1] 0.0312% EEA[2] | 114.375 | 0 | 25 | 174 |
| Example 5 | 1 | 0.0312% MPP[1] 0.0312% EEA[2] | 114.375 | 0.8 | 25.5 | 198 |

MPP[1] maleated polypropylene
EEA[2] ethylene acrylic acid copolymer

For Examples 4-5, samples were tested by the Oven Shake-Out Procedure as set forth herein. The superabsorbent composition shake-out of the Examples 4-5 was measured and is found in Table 4.

TABLE 4

Superabsorbent Composition Shake-out Results for Examples 4-5

| Examples | pan + film (g) | preshake (g) | post shake (g) | % SAP retained | % SAP shake-out |
|---|---|---|---|---|---|
| Ex 4a | 2.7971 | 3.6284 | 3.5854 | 94.83 | 5.17 |
| Ex 4b | 2.8346 | 4.03 | 3.8011 | 80.85 | 19.15 |
| Ex 5 | 2.8251 | 3.6555 | 3.55 | 87.30 | 12.70 |

What is claimed:

1. Thermoplastic polymer treated superabsorbent polymer particles comprising a superabsorbent polymer composition comprising a superabsorbent polymer comprising:
   a) from about 55 to about 99.9% by weight of the superabsorbent polymer of polymerizable unsaturated acid group containing monomer based on the superabsorbent polymer; and
   b) from about 0.001 to about 5% by weight of internal crosslinking agent based on the polymerizable unsaturated acid group containing monomer; wherein the superabsorbent polymer has a degree of neutralization of greater than about 25%; wherein elements a) and b) are polymerized and prepared into superabsorbent polymer particles further comprising the following surface additives to form surface treated superabsorbent polymer particles
   i) from about 0.001 to about 5% by weight of surface crosslinking agent based on the dry superabsorbent polymer composition;
   ii) from about 0.01 to about 10% by weight of the dry superabsorbent polymer composition of a penetration modifier selected from polyethylene glycols, tetraethylene glycol dimethyl ether, monovalent metal salts, surfactants, water soluble polymers, thermoplastic resins or blends thereof;
   iii) from 0 to about 5% by weight of a multivalent metal salt based on the dry superabsorbent polymer composition;
   iv) from 0 to about 2% by weight of a surfactant based on the dry superabsorbent polymer composition;
   v) from about 0.01 to about 1% by weight of an insoluble, inorganic powder based on the dry superabsorbent polymer composition; and
   vi) from about 0.01 to about 1% by weight of a thermoplastic polymer based on the dry superabsorbent polymer composition, wherein the thermoplastic polymer is a surface additive deposited on the superabsorbent polymer particles to form thermoplastic polymer treated superabsorbent polymer particles, wherein the thermoplastic polymer surface treated superabsorbent polymer particles are heat treated wherein the thermoplastic polymer of vi) is applied to the superabsorbent polymer particles prior to the heat treatment; and wherein the thermoplastic polymer surface treated superabsorbent polymer particles are sized in the range of from about 300 to about 600 microns, wherein the superabsorbent polymer particles further comprise a coating of from about 0.1 to about 5% by weight of a cationic polymer selected from poly(vinyl amines), poly(allylamines), poly(ethylene imine), poly(amino propanol vinyl ethers), poly(acrylamidopropyl trimethyl ammonium chloride), poly(diallyldimethyl ammonium chloride), partially deacetylated chitin, chitosan, polyaspargins, polylysines, polyglutamines, polyarginines, including salts thereof, based on the dry superabsorbent polymer composition, and wherein the thermoplastic polymer surface treated superabsorbent polymer particles exhibit a centrifuge retention capacity of at least about 23 g/g as measured by the Centrifuge Retention Capacity Test; a free swell gel bed permeability of at least 100 Darcy as measured by the Free Swell Gel Bed Permeability Test; and superabsorbent polymer composition shake-out of less than about 20% as measured by the Oven Shake-Out Procedure.

2. The thermoplastic polymer treated superabsorbent polymer particles according to claim 1 has a free swell gel bed permeability of at least about 130 Darcy.

3. The thermoplastic polymer treated superabsorbent polymer particles according to claim 1 has a free swell gel bed permeability of at least about 160 Darcy.

4. The thermoplastic polymer treated superabsorbent polymer particles according to claim 1 has a free swell gel bed permeability of at least about 200 Darcy.

5. The thermoplastic polymer treated superabsorbent polymer particles according to claim 1 wherein the superabsorbent polymer composition shake-out is less than about 16%.

6. The thermoplastic polymer treated superabsorbent polymer particles according to claim 1 comprising from about 0.1 to about 5% by weight of a multivalent metal salt based on the dry superabsorbent polymer composition.

7. The thermoplastic polymer treated superabsorbent polymer particles of claim 1 wherein the thermoplastic polymer is selected from the group consisting of polyolefin, polyethylene, polyesters, polyurethanes, linear low density polyethylene (LLDPE), ethylene acrylic acid copolymer (EAA), styrene copolymers, ethylene alkyl methacrylate copolymer (EMA), polypropylene (PP), maleated polypropylene (MPP), ethylene vinyl acetate copolymer (EVA), polyamide, polyester, and blends and copolymers thereof.

8. The thermoplastic polymer treated superabsorbent polymer particles of claim 1 having a gel bed permeability under load as measured by the Gel Bed Permeability Under Load Test of at least about 4 Darcy.

9. The thermoplastic polymer treated superabsorbent polymer particles of claim 1 having a gel bed permeability under load as measured by the Gel Bed Permeability Under Load Test of at least about 8 Darcy.

10. The thermoplastic polymer treated superabsorbent polymer particles of claim 1 having a gel bed permeability under load as measured by the Gel Bed Permeability Under Load Test of at least about 10 Darcy.

11. The thermoplastic polymer treated superabsorbent polymer particles of claim 1 having a centrifuge retention capacity of at least about 25 g/g.

12. The thermoplastic polymer treated superabsorbent polymer particles of claim 1 wherein the thermoplastic polymer is a maleated polypropylene.

13. Thermoplastic polymer treated superabsorbent polymer particles comprising a superabsorbent polymer composition comprising a superabsorbent polymer comprising:
   a) from about 55 to about 99.9% by weight of the superabsorbent polymer of polymerizable unsaturated acid group containing monomer based on the superabsorbent polymer; and
   b) from about 0.001 to about 5% by weight of internal crosslinking agent based on the polymerizable unsaturated acid group containing monomer; wherein the superabsorbent polymer has a degree of neutralization of greater than about 25%; wherein elements a) and b) are polymerized and prepared into superabsorbent polymer particles further comprising the following surface additives to form surface treated superabsorbent polymer particles
   i) from about 0.001 to about 5% by weight of surface crosslinking agent based on the dry superabsorbent polymer composition;
   ii) from 0 to about 5% by weight of a multivalent metal salt based on the dry superabsorbent polymer composition;
   iii) from 0 to about 2% by weight of a surfactant based on the dry superabsorbent polymer composition;
   iv) from about 0.01 to about 5% by weight of an insoluble, inorganic powder based on the dry superabsorbent polymer composition; and
   v) from about 0.01 to about 1% by weight of a thermoplastic polymer based on the dry superabsorbent polymer composition, wherein the thermoplastic polymer is a surface additive on the superabsorbent polymer particles, wherein the surface treated superabsorbent polymer particles are heat treated wherein the thermoplastic polymer of vi) is applied to the superabsorbent polymer particles prior to the heat treating the superabsorbent particles; and wherein the thermoplastic polymer surface treated superabsorbent polymer particles are sized in the range of from about 300 to about 600 microns, wherein the superabsorbent polymer particles further comprise a coating of from about 0.1 to about 5% by weight of a cationic polymer selected from poly(vinyl amines) and poly(allylamines), including salts thereof, based on the dry superabsorbent polymer composition, and wherein the thermoplastic polymer surface treated superabsorbent polymer particles exhibit a centrifuge retention capacity of at least about 23 g/g as measured by the Centrifuge Retention Capacity Test; a free swell gel bed permeability of at least 100 Darcy as measured by the Free Swell Gel Bed Permeability Test; and superabsorbent polymer composition shake-out of less than about 20% as measured by the Oven Shake-Out Procedure.

14. The thermoplastic polymer treated superabsorbent polymer particles according to claim 13 has a free swell gel bed permeability of at least about 130 Darcy.

15. The thermoplastic polymer treated superabsorbent polymer particles according to claim 13 wherein the superabsorbent polymer composition shake-out is less than about 16%.

16. The thermoplastic polymer treated superabsorbent polymer particles according to claim 13 comprising from about 0.1 to about 5% by weight of a multivalent metal salt based on the dry superabsorbent polymer composition.

17. The thermoplastic polymer treated superabsorbent polymer particles of claim 13 wherein the thermoplastic polymer is selected from the group consisting of polyolefin, polyethylene, polyesters, polyurethanes, linear low density polyethylene (LLDPE), ethylene acrylic acid copolymer (EAA), styrene copolymers, ethylene alkyl methacrylate copolymer (EMA), polypropylene (PP), maleated polypropylene (MPP), ethylene vinyl acetate copolymer (EVA), polyamide, polyester, and blends and copolymers thereof.

18. The thermoplastic polymer treated superabsorbent polymer particles of claim 13 having a gel bed permeability under load as measured by the Gel Bed Permeability Under Load Test of at least about 4 Darcy.

19. The thermoplastic polymer treated superabsorbent polymer particles of claim 13 having a centrifuge retention capacity of at least about 25 g/g.

20. The thermoplastic polymer treated superabsorbent polymer particles of claim 13 wherein the thermoplastic polymer is a maleated polypropylene.

21. The thermoplastic polymer treated superabsorbent polymer particles of claim 1 wherein the thermoplastic polymer is from about 0.01 to about 0.0625% by weight of a thermoplastic polymer based on the dry superabsorbent polymer composition.

22. The thermoplastic polymer treated superabsorbent polymer particles of claim 13 wherein the thermoplastic polymer is from about 0.01 to about 0.0625% by weight of a thermoplastic polymer based on the dry superabsorbent polymer composition.

23. The thermoplastic polymer treated superabsorbent polymer particles according to claim 1 comprising from about 0.01 to about 0.05% by weight of a thermoplastic polymer based on the dry superabsorbent polymer composition, wherein the thermoplastic polymer is a surface additive on the superabsorbent polymer particles.

24. The thermoplastic polymer treated superabsorbent polymer particles according to claim 13 comprising from about 0.01 to about 0.05% by weight of a thermoplastic polymer based on the dry superabsorbent polymer composition, wherein the thermoplastic polymer is a surface additive on the superabsorbent polymer particles.

25. The thermoplastic polymer treated superabsorbent polymer particles according to claim 1 wherein the cationic polymer is polyvinylamine.

26. The thermoplastic polymer treated superabsorbent polymer particles according to claim 13 wherein the cationic polymer is polyvinylamine.

* * * * *

UNITED STATES PATENT AND TRADEMARK OFFICE
CERTIFICATE OF CORRECTION

| | | |
|---|---|---|
| PATENT NO. | : 7,812,082 B2 | Page 1 of 1 |
| APPLICATION NO. | : 11/301359 | |
| DATED | : October 12, 2010 | |
| INVENTOR(S) | : Stan McIntosh et al. | |

It is certified that error appears in the above-identified patent and that said Letters Patent is hereby corrected as shown below:

Column 3,

Line 46, "Procedure of 5 less than" should read -- Procedure of less than --.

Line 67, "are intended 20 to" should read -- are intended to --.

Signed and Sealed this

Twenty-third Day of November, 2010

David J. Kappos
*Director of the United States Patent and Trademark Office*